(12) United States Patent
Crystal et al.

(10) Patent No.: US 6,939,540 B1
(45) Date of Patent: Sep. 6, 2005

(54) METHOD OF ENHANCING BONE DENSITY

(75) Inventors: Ronald G. Crystal, Potomac, MD (US); Chisa Hidaka, New York, NY (US); Oheneba Boachie-Adjei, New York, NY (US); Bernard A. Rawlins, Englewood, NJ (US); Imre Kovesdi, Rockville, MD (US)

(73) Assignees: Cornell Research Foundation, Inc., Ithaca, NY (US); The Hospital for Special Surgery, New York, NY (US); GenVec, Inc., Gaithersburg, MD (US)

( * ) Notice: Subject to any disclaimer, the term of this patent is extended or adjusted under 35 U.S.C. 154(b) by 0 days.

(21) Appl. No.: 09/629,074

(22) Filed: Jul. 31, 2000

(51) Int. Cl.[7] .................. A01N 63/00; A01N 43/04; A61K 48/00; C12N 5/00; C12N 15/00
(52) U.S. Cl. ................. 424/93.2; 424/93.1; 424/93.21; 435/320.1; 435/325; 435/455; 514/44
(58) Field of Search ............................ 435/320.1, 325, 435/455; 514/44; 424/93.1, 93.2, 93.21, 424/93.6

(56) References Cited

U.S. PATENT DOCUMENTS

| | | |
|---|---|---|
| 5,073,492 A | 12/1991 | Chen et al. |
| 5,219,739 A | 6/1993 | Fiddes et al. |
| 5,652,225 A | 7/1997 | Isner |
| 5,869,037 A | 2/1999 | Crystal et al. |
| 5,942,496 A | 8/1999 | Bonadio et al. ............... 514/44 |
| 6,040,157 A | 3/2000 | Hu et al. |
| 6,077,987 A * | 6/2000 | Breitbart et al. ............... 623/11 |

FOREIGN PATENT DOCUMENTS

| | | |
|---|---|---|
| EP | 0 327 960 A | 8/1988 |
| WO | WO 95/24473 A | 9/1995 |
| WO | WO 96/38168 A | 12/1996 |
| WO | WO 97/30155 A | 8/1997 |
| WO | WO 97/38729 A | 10/1997 |
| WO | WO 98/32859 A1 | 7/1998 |
| WO | WO 99/10525 A | 3/1999 |
| WO | WO 99/11664 A | 3/1999 |
| WO | WO 99/40197 A2 | 8/1999 |
| WO | WO 99/40197 A3 | 8/1999 |
| WO | 99-53943 * | 10/1999 |
| WO | WO 00/04183 A | 1/2000 |
| WO | WO 00/71713 A | 11/2000 |
| WO | WO 01/08714 A | 2/2001 |

OTHER PUBLICATIONS

Ferrara et al., Molecular and Biological Properties of the Vascular Endothelial Growth Factor Family of Proteins, 1992, Endocrine Reviews, vol. 13, No. 1, pp. 18-32.*
Neufeld et al., Vascular endothelial growth factor (VEGF) and its receptors, Jan. 1999, The FASEB Journal, vol. 13, pp. 9-22.*
Karsenty et al., The gentic transformation of bone biology, 1999, Genes and Development, vol. 13, pp. 3037-3051.*
Lee et al., The Effect of Recombinant Indian Hedgehog on Murine Fracture Repair, 2000, Orthopaedic Research Society, p. 0275.*
Crystal Transfer of genes to humans: early lessons and obstacles to success pp. 404-410 vol. 270 1995.*
Deonarain Ligand-targeted receptor-mediated vectors for gene delivery pp. 53-69 1998.*
Friedman Overcoming the obstacles pp. 96-101 1997.*
Gene therapy's growing pains pp. 1050-1055 vol. 269 1995.*
Miller et al. Targeted vectors for gene therapy pp. 190-199 1995.*
Verma et al. Gene therapy promises, problems and prospects pp. 239-242.*
Orkin, M.D. et al. Report and recommendations of the panel tro assess the NIH investment in research on gene therapy pp. 1-40 1995.*
McKusick et al. (2004) OMIM database entry for Transforming Growth Factor, Beta-1; TGFB1. p. 1 at http://www.ncbi.nlm.nih.gov/entrez/dispomim.cgi?id=190180.*
About.com, "Angiogenesis Inhibitors for Cancer Treatment: Drugs in Clinical Trials—Introduction and Background." (Nov. 9, 1998). [http://pharmacology.about.com/health/pharmacology/library/weekly/aa981109.htm].
Baltzer et al., *Gene Therapy*, 7, 734-739 (2000).
Baltzer et al., *Knee Surgery, Sports Traumatology, Arthropscopy*, 7, 197-202 (1999).
Batlzer et al., *Acta Orthop Scand*, 70 (5), 419-424 (1999).

(Continued)

*Primary Examiner*—Anne-Marie Falk
(74) *Attorney, Agent, or Firm*—Leydig, Voit & Mayer, Ltd.

(57) ABSTRACT

The present invention is directed to a method for enhancing bone density or formation. In accordance with the method, a nucleic acid encoding an angiogenic protein is administered to a cell in a region of a bone such that the nucleic acid is expressed to produce the angiogenic protein, whereby bone density or formation is enhanced within the region. Optionally, a nucleic acid encoding an osteogenic protein is administered to a cell within the same region such that the nucleic acid is expressed to produce the osteogenic protein. The method can be employed to produce a bone graft having a cell harboring an exogenous nucleic acid encoding an angiogenic protein and, optionally, a cell harboring a nucleic acid encoding an osteogenic protein. To facilitate the inventive method, the invention also pertains to a recombinant viral vector having a nucleic acid encoding an angiogenic protein and a nucleic acid encoding an osteogenic protein.

37 Claims, No Drawings

OTHER PUBLICATIONS

Boden et al., *Spine,* 23 (23), 2486-2492 (1998).
Bruder J. et al., *Journal of Virology,* 71 (10), 7623-7628 (1997).
Bruder S. et al., *Clinical Orthopaedics and Related Research,* 355S, S247-S256 (1998).
Day et al., *Tissue Engineering,* 5 (2), 119-125 (1999).
Eppley et al., *Journal of Oral and Maxillofacial Surgery,* 46, 397-398 (1988).
Gerber et al., *Nature Medicine,* 5 (6), 623-628 (1999).
Goldstein et al., *Clinical Orthopaedics and Related Research,* 355S, S154-S162 (1998).
Harada et al., *Journal of Clinical Investigations,* 93, 2490-2496 (1994).
Harper et al., *Nature Medicine,* 5 (6), 617-618 (1999).
Leunig et al., *International Journal of Microcirculation,* 17, 1-9 (1997).
Leunig et al., *Laboratory Investigation,* 71 (2), 300-307 (1994).
Ludwig et al., *Bone Grafting and Bone Graft Substitutes,* 30 (4), 635-645 (1999).
Ludwig et al., *European Spine Journal,* 9 (Suppl. 1), S119-S125 (2000).
Mehrara et al., *Journal of Bone and Mineral Research,* 14 (8), 1290-1301 (1999).
Morone et al., *Clinical Orthoaedics and Related Research,* 351, 252-265 (1998).
Nakagawa et al., *FEBS Letters,* 473, 161-164 (2000).
Niyibizi et al., *Clinical Orthopaedics and Related Research,* 355S, S148-S153 (1998).
Ohta et al., *Journal of Bone and Mineral Research,* 14 (7), 1132-1144 (1999).
Riew et al., *Calcified Tissue International,* 63, 357-360 (1998).
Saadeh et al., *American Journal of Physiology,* 277, C628-C637 (1999).
Stevenson, *Clinical Orthopaedics and Related Research,* 355S, S239-S246 (1998).
Vortkamp et al., *Science,* 273, 613-622 (1996).
Weiss et al., *The Journal of Hand Surgery,* 20A, 94-100 (1995).
Yeh et al., *Molecular and Cellular Endocrinology,* 153 (113-124 (1999).
Anh et al., *Calcif. Tissue Int.,* 62, 332-340 (1998).
Beck et al., "The role of the p300 and pRB families in regulating cell growth and tissue specific gene expression in osteoblast differentiation," *Presented at The 2000 Molecular Biology of DNA Tumor Virus Conference* (University of Wisconsin, Madison, Wisconsin, Jul. 8-13, 2000).
Berger et al., *Gene,* 66, 1-10 (1988).
Brough et al., *J. Virol.,* 71 (12), 9206-9213 (Dec. 1997).
Ducy et al., *Science,* 289, 1501-1504 (Sep. 1, 2000).
Iwamoto et al., *Crit. Rev. Oral Biol. Med.,* 10 (4), 477-486 (1999).
Karp et al., *Development,* 127, 543-548 (2000).
Kiberstis et al., *Science,* 289, 1497 (Sep. 1, 2000).
Kinto et al., *FEBS Lett.,* 404, 319-323 (1997).
Krezel et al., *Science,* 264, 1944-1947 (Jun. 24, 1994).
Lacey et al., *Cell,* 93, 165-176 (Apr. 17, 1998).
Manolagas et al., *J. Biol. Chem.,* 256 (14), 7115-7117 (Jul. 25, 1981).
Nakamura et al., *Biochem. Biophys. Res. Comm.,* 237, 465-469 (1997).
Rakopolous et al., *Bone,* 17 (5), 447-453 (Nov. 1995).
Rodan et al., *Science,* 289, 1508-1514 (Sep. 1, 2000).
Service, *Science,* 289, 1498-1500 (Sep. 1, 2000).
Simonet et al., *Cell,* 89, 309-319 (Apr. 18, 1997).
Teitelbaum, *Science,* 289, 1504-1508 (Sep. 1, 2000).
Wada et al., *Endocrinol.,* 137 (3), 1042-1048 (1996).

* cited by examiner

METHOD OF ENHANCING BONE DENSITY

TECHNICAL FIELD OF THE INVENTION

This invention pertains to a method and reagents for enhancing bone density or formation.

BACKGROUND OF THE INVENTION

Most attempts of enhancing bone density or formation have traditionally come in the form of increased support and/or the addition of bone graft material to the site of treatment. Such approaches, however, have had only limited success and often fail to provide aid to patients with bone healing deficiencies. For example, spinal fusion protocols typically employ bone autografts, which are fractured into small pieces and placed between the spinal processes to be fused. Such procedures achieve favorable results only in about 40% of treated patients, and the procedures for harvesting graft material render an already invasive procedure even more so.

Efforts to mimic and/or supplement the normal series of events underlying proper bone healing, and also to cure deficiencies associated with these events, have been forthcoming. For example, blood vessel growth has been stimulated in normally healing rabbit mandibular bones by mixing rabbit bone graft material ex vivo with basic fibroblast growth factor (bFGF) and endothelial cells prior to graft implantation (Eppley et al., *J. Oral Maxillofac. Surg.*, 46, 391–98 (1988)). Moreover, in efforts to accelerate fracture healing, osteoblasts and osseous tissue have been infected in vitro and in vivo with vectors delivering DNA encoding osteogenic proteins, such as transforming growth factor-$\beta 1$ and bone morphogenic protein-2 (Baltzer et al., *Gene Ther.*, 7, 734–79 (2000); Boden et al., *Spine*, 23, 2486–92 (1998); Gosdstein et al., *Clin. Orthopaed. Rel. Res.*, 355S, S154–62 (1998); Mehrara et al., *J. Bone Min. Res.*, 14(8), 1290–1300 (1999); Riew et al, *Calcif. Tissue Int.*, 63, 357–60 (1998)). However, many such proteins precipitate an inhibitory effect in treated tissues, and some discourage essential neovascularization within such tissues. Moreover, such protocols requiring treatment of rare cells, such as stem cells, depend on the isolation of sufficient quantities of such proteins, which can add yet another level of invasiveness to the procedure, increasing morbidity and post-operative pain and discomfort. Thus, despite improvements in the clinical treatment of bone injuries, there continues to exist a need for improved compositions and/or methods that enhance bone density or formation.

BRIEF SUMMARY OF THE INVENTION

One aspect of the invention pertains to a method for enhancing bone density or formation. In accordance with the method, a nucleic acid encoding an angiogenic protein is administered to a cell in a region of a bone such that the nucleic acid is expressed to produce the angiogenic protein, whereby bone density or formation is enhanced within the region. Optionally, a nucleic acid encoding an osteogenic protein is administered to a cell within the same region such that the nucleic acid is expressed to produce the osteogenic protein. The method can be employed to produce a bone graft having a cell harboring an exogenous nucleic acid encoding an angiogenic protein and, optionally, a cell harboring a nucleic acid encoding an osteogenic protein. To facilitate the inventive method, the invention provides a recombinant viral vector having a nucleic acid encoding an angiogenic protein and a nucleic acid encoding an osteogenic protein. These and other advantages, as well as additional inventive features, will become apparent after reading the following detailed description.

DETAILED DESCRIPTION OF THE INVENTION

In accordance with the inventive method, a nucleic acid is administered to a cell (e.g., at least one cell) associated with a desired region of a bone. The relevant "region" of the bone includes the bone itself as well as the immediately adjoining area within the bone or in tissues surrounding it (e.g., periosteum, muscle, fascia, tendons, ligaments, etc.). With this in mind, a cell is "associated with" the bone if it is within the region of the bone before, during, or following application of the inventive method. Any cell associated with the region of the bone can be treated in accordance with the inventive method to express exogenous nucleic acids to produce (and typically secrete) encoded proteins. Inasmuch as such cells are employed as bioreactors in the application of the method, the type of cell is not critical. Thus the cell generally is any cell type associated with bony structures. Thus, for example, the cell can be within the bone (e.g., a preosteocyte, an osteocyte, chondrocyte, stromal cell, etc.) or in other tissue adjoining the desired region (e.g., a periosteal or fascial cell, a muscle cell, etc.). Alternatively, a cell associated with the bone region can be initially away from the region and introduced into it during application of the method. For example, the cell can be within an exogenous tissue, such as a bone graft or other similar tissue, which is implanted or engrafted into the region of the bone.

The inventive method involves administering a nucleic acid (i.e., a first nucleic acid) encoding an angiogenic protein to a cell (i.e., a first cell) within the region of the bone. An angiogenic protein is any protein that potentiates or enhances neovascularization, many of which are known in the art. While any such factor can be employed in the context of the inventive method, because VEGF proteins are not known to induce the growth of tissues not involved in the production of new vasculature, a preferred angiogenic protein is a VEGF protein (e.g., $VEGF_A$, $VEGF_B$, $VEGF_C$, $VEGF_D$, $VEGF_E$), and more preferably $VEGF_{121}$, $VEGF_{A138}$, $VEGF_{145}$, $VEGF_{A162}$, $VEGF_{165}$, $VEGF_{182}$, $VEGF_{189}$, or a derivative thereof, (see, e.g., U.S. Pat. No. 5,332,671 (Ferrara et al.), U.S. Pat. No. 5,240,848 (Keck et al.); and U.S. Pat. No. 5,219,739 (Tischer et al.)). Most preferably, because of their higher biological activity, the angiogenic protein is $VEGF_{121}$ or $VEGF_{165}$, particularly $VEGF_{121}$. Inasmuch as $VEGF_{121}$ typically binds heparin with lesser affinity than does $VEGF_{165}$, $VEGF_{121}$ is particularly preferred for use in the inventive method. While VEGF proteins are preferable for use in the inventive method, other angiogenic proteins include connective tissue growth factor (CTGF), VEGF2, VEGF-C, fibroblast growth factors (FGFs) (e.g., aFGF, bFGF, and FGF4), angiopoiteins, angiopoetin homologous proteins, angiogenin, angiogenin-2, and P1GF (see, e.g., U.S. Pat. Nos. 5,194,596, 5,219,739, 5,338, 840, 5,532,343, 5,169,764, 5,650,490, 5,643,755, 5,879,672, 5,851,797, 5,843,775, and 5,821,124; International Patent Application WO 95/24473; European Patent Documents 476 983, 506 477, and 550 296; Japanese Patent Documents 1038100, 2117698, 2279698, and 3178996; and J. Folkman et al., *A Family of Angiogenic Proteins*, Nature, 329, 671 (1987)).

To enhance the efficacy of the inventive method, a nucleic acid (i.e., second nucleic acid) encoding an osteogenic protein can be similarly delivered to a cell (i.e., a second cell) within the same region of the bone. An osteogenic protein is any protein that potentiates or enhances ossification or differentiation of bone, many of which are known in the art. Osteogenic proteins include, for example, systemic hormones, (e.g., parathyroid hormone (PTH) estrogen, etc.), growth factors (e.g., CTGF and CTGF-like growth factor), cytokines, chemotactic and adhesive proteins, molecules such as activin (U.S. Pat. No. 5,208,219), bone morphogenic proteins (BMPs), growth factor receptors, and the like. Preferably, the osteogenic protein of the present invention is selected a bone morphogenic protein (BMP) (e.g., BMP-2, BMP-3, BMP-4, BMP-5, BMP-6, BMP-7 and BMP-8), a transforming growth factor (TGF) (e.g., TGF-β1), a latent TGF binding protein (LTBP), latent membrane protein-1 (LMP-1), a heparin-binding neurotrophic factor (HBNF), growth and differentiation factor-5 (GDF-5), a parathyroid hormone (PTH), a fibroblast growth factor (FGF), an epidermal growth factor (EGF), a platelet-derived growth factor (PDGF), an insulin-like growth factor (e.g., IGF-1 or 2)), a growth factor receptor, a cytokine, a chemotactic factor, a granulocyte/macrophage colony stimulating factor (GMCSF), a LIM mineralization protein (LMP) (Boden et al., *Spine,* 23, 2486–92 (1998)), a leukemia inhibitory factor (LIF), a hedgehog protein (e.g., Desert Hedgehog (DHH), Indian Hedgehog (1HH), Sonic Hedgehog, etc.) or a derivative thereof. Most preferably, the osteogenic protein is TGF-β1 or midkine (MK) and, as discussed above, these are preferably employed where the angiogenic factor is a VEGF. Some osteogenic proteins also can stimulate the growth or regeneration of skeletal connective tissues such as, e.g., tendon, cartilage, ligament, etc.

While the sequences of many angiogenic and osteogenic proteins, and nucleic acids encoding them, are known, any active derivative sequence can be employed in the place of known sequences. These derivatives include those caused by point mutations, those due to the degeneracies of the genetic code or naturally occurring allelic variants, and further modifications that have been introduced by genetic engineering.

Where a nucleic acid encoding an angiogenic protein and a nucleic acid encoding an osteogenic protein (i.e., first and second nucleic acids) are both employed in the inventive method, they can be delivered to the same or different cells associated with the region of the bone. In this respect the first cell and the second cell can be the same cells or different cells. The method is more efficacious if the nucleic acid(s) are delivered to many cells associated with the region of the bone, such as a population of cells, or a majority of cells within the region. In any event, within at least the first cell, the first nucleic acid is expressed, leading to the production of the angiogenic protein. Desirably, a second nucleic acid is employed to similarly lead to the production of an osteogenic protein. Typically the encoded protein(s) is secreted from the cell, but it need not be. The presence of the angiogenic (and desirably osteogenic) protein promotes physiological changes within the region of the bone so as to enhance bone density or formation.

Successful application of the inventive method enhances bone density or formation in any respect. Thus, it is to be understood that the inventive method can strengthen or harden a region of contiguous bone. In other applications, enhancement of bone density or formation is associated with healing (e.g., fusion) of splintered or fractured bone. Similarly, the inventive method can facilitate fusion of two bone masses, such as a bone graft to a bony region within a patient or the fusion of separate bones within a patient, such as vertebrae or other desired bony structures. Moreover, in certain embodiments, the inventive method can be employed to stimulate the growth or repair of both bone tissue itself and also of skeletal connective tissues that surround or are associated with bone. Thus, the method can facilitate the attachment of such bone-associated tissues (e.g., ligaments) to bones.

A nucleic acid employed in the inventive method can be any suitable type sufficient to lead to the production of the desired protein within the cell(s) associated with the desired region of bone. In this respect, a nucleic acid can be RNA, cDNA, genomic DNA, etc., but typically it is cDNA, such as, for example, within an expression cassette. Moreover, in embodiments in which a polynucleotide encoding an osteogenic protein is delivered in conjunction with the nucleic acid encoding the angiogenic protein, the two nucleic acids can be present in the same molecule or on separate molecules (i.e., the first nucleic acid and the second nucleic acid can be the same). Of course, inasmuch as these nucleic acids can be delivered to different cells (i.e., first and second cells), it is quite possible for the two coding nucleic acids to be present on separate molecules.

Where a nucleic acid for use in the inventive method is within an expression cassette, the cassette also should have promoter able to drive the expression of the coding sequence within the cells. Many viral promoters are appropriate for use in such an expression cassette (e.g., retroviral ITRs, LTRs, immediate early viral promoters (IEp) (such as herpesvirus IEp (e.g., ICP4—IEp and ICP0-IEp) and cytomegalovirus (CMV) IEp), and other viral promoters (e.g., late viral promoters, latency-active promoters (LAPs), Rous Sarcoma Virus (RSV) promoters, and Murine Leukemia Virus (MLV) promoters)). Other suitable promoters are eukaryotic promoters, such as enhancers (e.g., the rabbit β-globin regulatory elements), constitutively active promoters (e.g., the β-actin promoter, etc.), signal specific promoters (e.g., inducible and/or repressible promoters, such as a promoter responsive to TNF or RU486, the metallothionine promoter, etc.), and tissue-specific promoters. Moreover, where the first and second nucleic acids are part of the same molecule, their respective cassettes can share a bi-directional promoter, many of which are known in the art (see, e.g., Lee et al., *Mol Cells.,* 10(1), 47–53 (2000), Dong et al., *J. Cell. Biochem.,* 77(1), 50–64 (2000), and Li et al., *J. Cell. Biochem.,* 273(43), 28170–77 (1998)), such that the respective coding sequences can be on opposite strands of the molecule.

Regardless of the type of promoter employed, within the expression cassette, the coding polynucleotide and the promoter are operably linked such that the promoter is able to drive the expression of the desired sequence. As long as this operable linkage is maintained, the expression cassette can include more than one gene, such as multiple coding sequences (e.g., the first and the second nucleic acids, as discussed herein) separated by ribosome entry sites. Furthermore, the expression cassette can optionally include other elements, such as polyadenylation sequences, transcriptional regulatory elements (e.g., enhancers, silencers, etc.), or other sequences.

For successful application of the inventive method, a nucleic acid encoding the angiogenic and/or the osteogenic protein must be introduced into a cell associated with the desired region of the bone in a manner suitable for it to express the encoded sequence. Any suitable vector can be employed to this end, many of which are known in the art. Examples of such vectors include naked RNA and DNA vectors (such as oligonucleotides, artificial chromosomes (e.g., yeast artificial chromosomes (YACs)), cosmids, plasmids, etc.), viral vectors such as adeno-associated viral vectors (Berns et al., *Ann. N.Y. Acad. Sci.*, 772, 95–104 (1995)), adenoviral vectors (Bain et al., *Gene Therapy*, 1, S68 (1994)), herpesvirus vectors (Fink et al., *Ann. Rev. Neurosci.*, 19, 265–87 (1996), U.S. Pat. Nos. 5,837,532; 5,846,782; 5,849,572; and 5,804,413 and International Patent Applications WO 91/02788, WO 96/04394, WO 98/15637, and WO 99/06583), packaged amplicons (Federoff et al., *Proc. Nat. Acad. Sci. USA*, 89, 1636–40 (1992)), pappiloma virus vectors, phage vectors, picornavirus vectors, polyoma virus vectors, retroviral vectors, SV40 viral vectors, vaccinia virus vectors, and other vectors. While some of the indicated vectors are suitable for use only with certain types of polynucleotides (e.g., cDNA as opposed, for example, to RNA), the selection of an appropriate vector and the use thereof to introduce exogenous genetic material (e.g., the desired nucleic acids) into cells are within the skill of the art. Once a given type of vector is selected, its genome must be manipulated for use as a background vector, after which it must be engineered to incorporate exogenous polynucleotides. Methods for manipulating the genomes of vectors are well known in the art (see, e.g., Sambrook et al., *Molecular Cloning. A Laboratory Manual*, 2d edition, Cold Spring Harbor Press (1989); Ausubel et al., *Current Protocols in Molecular Biology*, Greene Publishing Associates and John Wiley & Sons, New York, N.Y. (1994)) and include direct cloning, site specific recombination using recombinases, homologous recombination, and other suitable methods of constructing a recombinant vector. In this manner, an expression cassette can be inserted into any desirable position of the vector. Moreover, in addition to the desired expression cassette, a vector also can include other genetic elements as appropriate, such as, for example, genes encoding a selectable marker (e.g., β-gal or a marker conferring resistance to a toxin, such as puromycin or other similar selectable markers), a pharmacologically active protein, a transcription factor, or other biologically active substance.

As mentioned, within the context of the inventive method, one or more of the nucleic acids can be delivered to the cells as (i.e., within) a viral vector. To facilitate such embodiments of the method, the invention provides a viral vector having a first nucleic acid encoding an angiogenic protein and a second nucleic acid encoding an osteogenic protein, such as the angiogenic and osteogenic proteins discussed herein. While the inventive viral vector can be any suitable type of virus, adenoviral vectors present several advantages, particularly for in vivo applications, not the least of which is that the knowledge of such vector has advanced to a stage where virulence can be eliminated, tropism can be altered, exogenous genetic material can be introduced into such viral backbone, and the virus can be efficiently constructed, grown, purified, and stored (see, e.g., U.S. Pat. Nos. 6,063, 627, 6,057,155, 6,013,638, 5,997,509, 5,994,106, 5,965,541, 5,965,358, 5,962,311, 5,928,944, 5,869,037, 5,851,806, 5,849,561, 5,846,782, 5,837,511, 5,801,030, 5,770,442, 5,731,190, 5,712,136, and 5,559,099; International Patent Applications WO00/34496, WO00/34444, WO00/23088, WO00/15823, WO00/12765, WO00/00628, WO99/55365, WO99/54441, WO99/41398, WO99/23229, WO99/15686, WO98/56937, WO98/54346, WO98/53087, WO98/40509, WO98/32859, WO98/07877, WO98/07865, WO97/49827, WO97/21826, WO97/20051, WO97/12986, WO97/09439 and WO 96/26281, WO 96/07734, WO 95/34671; and European Patent Documents 0863987, 0866873, 0870049, 0914459, 0920524, 0973927, 0988390, 0996735, 1012291, 1015620). Indeed, recombinant adenoviruses having angiogenic genes are known in the art (see, e.g., Mack et al, *J. Thorac. Cardiobvasc. Surg.*, 115(1), 168–76 (1998);

Magovern et al., *Hum. Gene. Ther.*, 8(2), 215–27 (1997)), and a nucleic acid encoding an osteogenic protein can be cloned into such a backbone vector by standard methods.

Given the state of the art, an adenoviral vector of the present invention can be derived from any desired serotype of adenovirus. Adenoviral stocks that can be employed as a source of adenovirus can be amplified from the adenoviral serotypes 1 through 51, which are currently available from the American Type Culture Collection (ATCC, Rockville, Md.), or from any other serotype of adenovirus available from any other source. For instance, an adenovirus can be of subgroup A (e.g., serotypes 12, 18, and 31), subgroup B (e.g., serotypes 3, 7, 11, 14, 16, 21, 34, and 35), subgroup C (e.g., serotypes 1, 2, 5, and 6), subgroup D (e.g., serotypes 8, 9, 10, 13, 15, 17, 19, 20, 22–30, 32, 33, 36–39, and 42–47), subgroup E (serotype 4), subgroup F (serotypes 40 and 41), or any other adenoviral serotype. Preferably, however, an adenovirus is of serotype 2, 5 or 9.

Typically, aside from containing the sequences encoding the osteogenic and angiogenic proteins, the viral vector is deficient in at least one essential gene function. Such manipulations generally render the vector unable to replicate except in cells engineered to provide the missing essential gene function(s). For example, an adenoviral vector can have at least a partial deletion of the E1 (e.g., E1 a or E1 b), E2 and/or E4 regions, and desirably such a virus has a deletion in two, three or even all of these regions. Suitable replication-deficient adenoviral vectors are disclosed in U.S. Pat. Nos. 5,851,806 and 5,994,106 and International Patent Applications WO 95/34671 and WO 97/21826. Indeed, in preferred embodiments, at least one of the exogenous nucleic acids (e.g., encoding the osteogenic or the angiogenic proteins) is cloned into the E1 region of the adenoviral backbone, desirably oriented from "right to left" within the genome. While not essential for viral replication, the inventive adenoviral vector also can have at least a partial deletion in the E3 region as well.

In addition to a deficiency in the E1, E2, E3, and/or E4 region, an adenoviral vector according to the invention also can have a mutation in the major late promoter (MLP), for example in one or more control element(s) such that it alters the responsiveness of the promoter. Moreover, the tropism of viral vectors can be altered, for example by incorporating chimeric coat proteins into a viral surface that contains ligands able to mediate viral attachment to novel cell surfaces (e.g., either directly or through a bi- or multi-specific molecule) and/or by destroying the native tropism of the virus. Where the tropism of the virus is altered from that of the source virus, preferably it is engineered to contain a ligand conferring the ability to bind cells associated with bone tissue, such as, for example, osteocytes, chondrocytes, periosteal cells, myocytes, and cells in muscle and tendons that are associate with the type of bone to be treated. Many such ligands are known, and techniques for generating replication deficient adenoviral vectors and for altering viral tropism are well known in the art.

In application, the first and/or second nucleic acids (or a virus containing them, if appropriate) are delivered to the cell within a physiologically-acceptable solution.

Accordingly, to facilitate the inventive method, the invention provides a pharmaceutical (including pharmacological) composition including a first nucleic acid encoding an angiogenic protein, a second nucleic acid encoding an osteogenic protein (which can, of course, be within a recombinant virus as described herein), and a diluent. The diluent can include one or more pharmaceutically- (including pharmacologically- and physiologically-) acceptable carriers. For compositions suitable for in vitro application, the diluent can be a suitable tissue culture medium. Pharmaceutical compositions for use in accordance with the present invention can be formulated in any conventional manner using one or more pharmaceutically- or physiologically-acceptable carriers comprising excipients, as well as optional auxiliaries which facilitate processing of the nucleic acids into preparations which can be used pharmaceutically. Proper formulation is dependent upon the route of administration chosen. Thus, for systemic injection, the nucleic acids can be formulated in aqueous solutions, preferably in physiologically-compatible buffers. The nucleic acids can be formulated for parenteral administration by injection, e.g., by bolus injection or continuous infusion. Such compositions can take such forms as suspensions, solutions or emulsions in oily or aqueous vehicles, and can contain formulatory agents such as suspending, stabilizing and/or dispersing agents. For application to bony tissues, a preferred composition includes a porous or spongy matrix, such as collagen, which can be soaked or perfused with a fluid or semifluid carrier (e.g., buffered saline solution) including the nucleic acid(s). Such a matrix material assists in retaining the nucleic acid(s)s within the site of the bone to be treated. Of course, the nucleic acids also can be formulated into other compositions appropriate to the vector type such as those known in the art. Thus, for example, the nucleic acids could be administered in combination with further agents, such as, e.g., liposomes, lipids (e.g., cationic or anionic lipids), polypeptides, or various pharmaceutically active agents. In some embodiments, the nucleic acids can be delivered along with various other agents, such as an angiogenic factor and/or an inhibitor of bone resorption (see, e.g., U.S. Pat. Nos. 5,270,300 and 5,118,667).

The composition(s) containing the nucleic acids (or viral vector containing them) is delivered to tissue associated with the region of bone to be treated at any dose appropriate to enhance bone density or formation within the region. The appropriate dose will vary according to the type of vector employed, but it is within routine skill to select an suitable dosage. Thus, for example, where the nucleic acids are within an adenoviral vector, a dose typically will be at least about $1 \times 10^5$ pfu (e.g., $1 \times 10^6 - 1 \times 10^{12}$ pfu) to the site of administration. The dose preferably is at least about $1 \times 10^7$ pfu (e.g., about $1 \times 10^7 - 1 \times 10^{12}$ pfu), more preferably at least about $1 \times 10^8$ pfu (e.g., about $1 \times 10^8 - 1 \times 10^{11}$ pfu), and most preferably at least about $1 \times 10^9$ pfu (e.g., about $1 \times 10^9 - 1 \times 10^{10}$ pfu). For purposes of considering the dose in terms of particle units (pu), also referred to as viral particles, typically within about an order of magnitude of from about 10 to about 100 particles is equivalent to about 1 pfu (e.g., $1 \times 10^{12}$ pfu is roughly equivalent to $1 \times 10^{14}$ pu). In a single round of vector administration, using, for example, an adenoviral vector deleted of the E1 a region, part of the E1 b region, and part of the E3 region of the adenoviral genome, wherein the vector carries human $VEGF_{121}$ or $VEGF_{165}$ under the control of a standard CMV immediate early promoter, about $10^7 - 10^{12}$ pfu, preferably about $10^9 - 10^{10}$ pfu, are administered to the desired region. Of course, the amount of virus administered can vary depending on the volume of the area to be treated.

The composition is administered to the region of the bone in an appropriate manner to deliver the nucleic acids to the tissue. For application in vivo, the region of the bone is exposed, and the composition is delivered, so as to be in physical contact with the tissues within the region. While in some applications it is desirable to expose the bone itself, in other applications tissue surrounding or otherwise associated with the bone can be retained intact, with the composition delivering the nucleic acids to cells existing within such tissues. Inasmuch as the method can be employed in conjunction with standard surgical techniques, its application can be directed to serve any desired treatment goal. For example, the method can be employed to promote fracture repair by delivering the composition to the region of the fracture. Alternatively, the method can be employed with methods for bone fusion (e.g., vertebral fusion).

For application in vitro, such as on a bone graft, the bone material can be bathed in a composition containing the nucleic acids or, where appropriate, the bone material can be perfused with the composition. The period of such bathing or perfusion should be sufficient so as to permit the cell or cells to take up the nucleic acids. Depending on the desired use of the graft and the genetic constructs employed (e.g., inducible promoters, etc.), the cells need not be induced to express the nucleic acids in vitro.

Where the method is employed in vitro, it can be used to create bone grafts for tissue repair. Accordingly, the invention provides a bone graft having a first cell (preferably a population of cells) having a first exogenous nucleic acid encoding an angiogenic protein and optionally a second cell (preferably a population of cells) having a second nucleic acid encoding an osteogenic protein, such as are set forth above. Within the graft, the first and second cells can be the same, as can the first and second nucleic acids. The graft can be obtained from any suitable donor source according to commonly employed surgical techniques, the iliac crest being a common source of tissue for bone grafts. Alternatively, the graft can be grown de novo (e.g., from osteocytes, preosteocytes, stem cells, cartilage, etc.) prior to treatment. In this respect, the graft can be an autograft, derived from any desirable bony structure in the patient to whom the graft is to be re-implanted. In other applications, the graft can be an allograft or even a xenograft. Indeed, such graft tissue can be preserved for use in future applications, e.g., through incubation in culture medium, refrigeration, cryopreservation, etc. In any event, after the nucleic acids have been transferred to a cell or cells within the graft, it is implanted into a patient according to standard surgical techniques. Where the graft is other than an autograft, however, appropriate immunosupression should be employed as necessary to mitigate graft rejection. The cell(s) within the graft to which the nucleic acids have been transferred should express the nucleic acids to produce the angiogenic and osteogenic proteins at least after the graft has been implanted into the patient. As discussed, the presence of such proteins within the region of the fissure between the graft and the host tissue will facilitate fusion of the graft to the host bone.

EXAMPLE

While one of skill in the art is fully able to practice the instant invention upon reading the foregoing detailed description, the following example will help elucidate some of its features. In particular, it demonstrates that the transfer of a nucleic acid encoding an angiogenic or osteogenic protein to cells associated with a region of bone can increase bone density or formation and facilitate fusion of separate bony structures. As this example is presented for purely illustrative purposes, it should not be used to construe the scope of the invention in a limited manner, but rather it should be seen as expanding upon the foregoing description of the invention as a whole.

The procedures described in this example were conducted on 250 g Sprague-Dawley rats. Recombinant adenoviral vectors were constructed having either the E. coli β-galactosidase gene (Adβgal) or the VEGF$_{121}$ or VEGF$_{165}$ isoforms (AdVEGF$_{121}$, and AdVEGF$_{165}$). All adenovirus vectors were E1$^-$, partial E3$^-$ and based on the Ad5 genome, with transgenes in the E1 position under the CMV promoter/enhancer. (Mack et al., J. Thorac. Cardiobvasc. Surg., 115(1), 168–76 (1998); Magovern et al., Hum. Gene. Ther., 8(2), 215–27 (1997)).

Single level posterior lumbar arthrodesis was attempted in 30 rats. Left and right L4 and L5 transverse processes were exposed through a paraspinal muscle-splitting approach and then decorticated using scalpel blade. HELISTAT (COLLA-TEC, Plainsboro, N.J., USA) bovine collagen sponges were soaked with saline alone (75 μl/side) or saline with the various adenoviral vectors ($10^{-10}$ particle units/site). The treated sponges were inserted between the decorticated L4 and L5 transverse processes on both left and right sides.

In one experiment, conducted on 30 rats, three rats received no graft, 5 received saline alone, 6 received Adβgal, 7 received AdVEGF$_{121}$, 6 received AdVEGF$_{165}$, and 3 received a preparation of recombinant VEGF$_{165}$ (5 μl/side, R&D, Minneapolis, Minn., USA). In a second experiment, three groups of three rats each were treated by the AdVEGF$_{121}$ or AdVEGF$_{121}$, Adβgal, or saline. In each experiment, the spines were harvested 4 wks post-operatively and evaluated by gross inspection, high-resolution radiographs, and microscopic examination of H&E-stained decalcified histological specimens. Radiographs were assessed by three blinded observers.

In the first experiment, upon gross inspection new bone formation was evident in 4 sites (29% of sites) treated with AdVEGF$_{121}$, 4 sites (33% of sites) treated with AdVEGF$_{165}$. No gross evidence of bone was noted in spines treated with no carrier, no virus (saline alone), control virus (Adβgal) or recombinant VEGF protein. Radiographs revealed an increase in the formation of radio-dense bone between L4 and L5 transverse processes in spines treated with AdVEGF ($_{121}$ or $_{165}$) when compared to controls. Specimens with radiographic evidence of new bone formation also showed the presence of tissue with the histological appearance of new woven bone was contiguous with the L4 or L5 transverse processes. In the second experiment, 3 sites (50% of sites) treated with the AdVEGF vectors showed the presence of bone growth between the processes, while no bone growth was observed with the Adβgal or saline controls. Similar results (50% of treated sites) were observed in animals treated with an adenoviral vector having the coding sequence encoding bone morphogenic protein-1 (AdBMP).

Incorporation by Reference

All sources (e.g., inventor's certificates, patent applications, patents, printed publications, repository accessions or records, utility models, world-wide web pages, and the like) referred to or cited anywhere in this document or in any drawing, Sequence Listing, or Statement filed concurrently herewith are hereby incorporated into and made part of this specification by such reference thereto.

Interpretation Guidelines

The foregoing detailed description sets forth "preferred embodiments" of this invention, including the best mode known to the inventors for carrying it out. Of course, upon reading the foregoing description, variations of those preferred embodiments will become obvious to those of ordinary skill in the art. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law.

As used herein, singular indicators (e.g., "a" or "one") include the plural, unless otherwise indicated. The term "consisting essentially of" indicates that unlisted ingredients or steps that do not materially affect the basic and novel properties of the invention can be employed in addition to the specifically recited ingredients or steps. In contrast, the terms "comprising" or "having" indicate that any ingredients or steps can be present in addition to those recited. The term "consisting of" indicates that only the recited ingredients or steps are present, but does not foreclose the possibility that equivalents of the ingredients or steps can substitute for those specifically recited.

What is claimed is:

1. A method for enhancing bone density or formation, the method comprising (a) administering to at least one first cell within a bone or within a tissue immediately surrounding a bone an adenoviral vector comprising at least one first nucleic acid encoding a VEGF 121, and (b) administering to at least one second cell within the bone or within a tissue immediately surrounding the bone an adenoviral vector comprising at least one second nucleic acid encoding at least one osteogenic protein, wherein the osteogenic protein is selected from the group consisting of a latent TGF binding protein (LTBP), latent membrane protein-1(LMP-1), a heparin-binding neurotrophic factor (HBNF), a parathyroid hormone (PTH), a growth factor receptor, a LIM mineralization protein (LMP), a hedgehog protein, and midkine (MK), such that the first nucleic acid is expressed in the first cell to produce the vascular endothelial growth factor, and the second nucleic acid is expressed in the second cell to produce the osteogenic protein, whereby bone density or formation is enhanced within the region.

2. The method of claim 1, wherein the adenoviral vector is exposed to at least one cell in vivo in the region of the bone.

3. The method of claim 1, wherein the adenoviral vector is exposed to at least one cell ex vivo, which is then delivered in vivo to the region of the bone.

4. The method of claim 1, wherein the osteogenic protein is MK.

5. The method of claim 1, wherein the osteogenic protein is HBNF.

6. The method of claim 1, wherein the first cell and the second cell are the same cell.

7. An adenoviral vector comprising at least one first nucleic acid encoding a vascular endothelial growth factor VEGF 121 and at least one second nucleic acid encoding at least one osteogenic protein, wherein the osteogenic protein is selected from the group consisting of a latent TGF binding protein (LTBP), latent membrane protein-1 (LMP-1), a heparin-binding neurotrophic factor (HBNF), a parathyroid hormone (PTH), a growth factor receptor, a LIM mineralization protein (LMP), a hedgehog protein, and midkine (MK).

8. The adenoviral vector of claim 7, which is deficient in at least one essential gene function.

9. A bone graft comprising at least one first cell having at least one first exogenous nucleic acid encoding a vascular endothelial growth factor VEGF 121 and at least one second cell having at least one second nucleic acid encoding at least one osteogenic protein, wherein the osteogenic protein is selected from the group consisting of a latent TGF binding protein (LTBP), latent membrane protein-1 (LMP-1), a heparin-binding neurotrophic factor (HBNF), a parathyroid hormone (PTH), a growth factor receptor, a LIM mineralization protein (LMP), a hedgehog protein, and midkine (MK).

10. The bone graft of claim 9, which is an allograft.

11. The bone graft of claim 9, wherein the osteogenic protein is MK.

12. The bone graft of claim 9, wherein the osteogenic protein is HBNF.

13. The adenoviral vector of claim 7, wherein the osteogenic protein is MK.

14. The adenoviral vector of claim 7, wherein the osteogenic protein is HBNF.

15. A method for enhancing bone density or formation, the method comprising administering to at least one first cell within a bone or within a tissue immediately surrounding a bone an adenoviral vector comprising at least one first nucleic acid encoding a vascular endothelial growth factor, and administering to at least one second cell within the bone or within a tissue immediately surrounding the bone an adenoviral vector comprising at least one second nucleic acid encoding at least one osteogenic protein, wherein the osteogenic protein is a heparin-binding neurotrophic factor (HBNF) or midkine (MK), such that the first nucleic acid is expressed in the first cell to produce the vascular endothelial growth factor, and the second nucleic acid is expressed in the second cell to produce the osteogenic protein, whereby bone density or formation is enhanced within the region.

16. The method of claim 15, wherein the vascular endothelial growth factor is selected from the group consisting of VEGF 121, VEGF 165, VEGFA 138, VEGFA 162, VEGF 182, VEGF 189, and VEGF-C.

17. The method of claim 15, wherein the osteogenic protein is MK.

18. The method of claim 15, wherein the osteogenic protein is HBNF.

19. The method of claim 15, wherein the adenoviral vector is exposed to at least one cell in vivo in the region of the bone.

20. The method of claim 15, wherein the adenoviral vector is exposed to at least one cell ex vivo, which is then delivered in vivo to the region of the bone.

21. The method of claim 15, wherein the first cell and the second cell are the same cell.

22. An adenoviral vector comprising at least one first nucleic acid encoding a vascular endothelial growth factor and at least one second nucleic acid encoding at least one osteogenic protein, wherein the osteogenic protein is a heparin-binding neurotrophic factor (HBNF) or midkine (MK).

23. The adenoviral vector of claim 22, wherein the vascular endothelial growth factor is selected from the group consisting of VEGF 121, VEGF 165, VEGFA 138, VEGFA 162, VEGF 182, VEGF 189, and VEGF-C.

24. The adenoviral vector of claim 22, wherein the osteogenic protein is MK.

25. The adenoviral vector of claim 22, wherein the osteogenic protein is HBNF.

26. The adenoviral vector of claim 22, which is deficient in at least one essential gene function.

27. A bone graft comprising at least one first cell having at least one first exogenous nucleic acid encoding a vascular endothelial growth factor and at least one second cell having at least one second nucleic acid encoding at least one osteogenic protein, wherein the osteogenic protein is a heparin-binding neurotrophic factor (HBNF) or midkine (MK).

28. The bone graft of claim 27, wherein the vascular endothelial growth factor is selected from the group consisting of VEGF 121, VEGF 165, VEGFA 138, VEGFA 162, VEGF 182, VEGF 189, and VEGF-C.

29. The bone graft of claim 27, wherein the osteogenic protein is MK.

30. The bone graft of claim 27, wherein the osteogenic protein is HBNF.

31. The bone graft of claim 27, which is an allograft.

32. The method of claim 1, wherein the osteogenic protein is selected from the group consisting of a latent TGF binding protein (LTBP), latent membrane protein-1 (LMP-1), and a parathyroid hormone.

33. The method of claim 1, wherein the osteogenic protein is selected from the group consisting of a growth factor receptor, a LIM mineralization protein (LMP), and a hedgehog protein.

34. The adenoviral vector of claim 7, wherein the osteogenic protein is selected from the group consisting of a latent TGF binding protein (LTBP), latent membrane protein-1 (LMP-1), and a parathyroid hormone.

35. The adenoviral vector of claim 7, wherein the osteogenic protein is selected from the group consisting of a growth factor receptor, a LIM mineralization protein (LMP), and a hedgehog protein.

36. The bone graft of claim 9, wherein the osteogenic protein is selected from the group consisting of a latent TGF binding protein (LTBP), latent membrane protein-1 (LMP-1), and a parathyroid hormone.

37. The bone graft of claim 9, wherein the osteogenic protein is selected from the group consisting of a growth factor receptor, a LIM mineralization protein (LMP), and a hedgehog protein.

* * * * *